United States Patent
Kim et al.

(10) Patent No.: US 12,323,076 B2
(45) Date of Patent: Jun. 3, 2025

(54) ULTRASONIC WAVE-DRIVEN TRIBOELECTRIC GENERATOR WITH SELF-GAP FORMED USING PLASMA ETCHING

(71) Applicant: RESEARCH & BUSINESS FOUNDATION SUNGKYUNKWAN UNIVERSITY, Suwon-si (KR)

(72) Inventors: SangWoo Kim, Yongin-si (KR); Young Jun Kim, Daejeon (KR); Young Wook Chung, Suwon-si (KR); Joon Ha Hwang, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 355 days.

(21) Appl. No.: 17/974,640

(22) Filed: Oct. 27, 2022

(65) Prior Publication Data

US 2023/0135593 A1    May 4, 2023

(30) Foreign Application Priority Data

Oct. 29, 2021    (KR) .................. 10-2021-0146182

(51) Int. Cl.
| | | |
|---|---|---|
| *H02N 1/04* | (2006.01) | |
| *A61N 1/36* | (2006.01) | |
| *A61N 1/378* | (2006.01) | |
| *A61N 7/00* | (2006.01) | |

(52) U.S. Cl.
CPC ............. *H02N 1/04* (2013.01); *A61N 1/3605* (2013.01); *A61N 1/378* (2013.01); *A61N 2007/0021* (2013.01)

(58) Field of Classification Search
CPC ........ H02N 1/04; A61N 1/3605; A61N 1/378; A61N 2007/0021
See application file for complete search history.

(56) References Cited

U.S. PATENT DOCUMENTS

2016/0156282 A1*  6/2016  Lee ..................... A61N 1/0484
                                                                607/61
2021/0170169 A1*  6/2021  Kim ......................... H02N 1/04

FOREIGN PATENT DOCUMENTS

CN           109149997 A  *  1/2019  ............ B82Y 30/00
KR    10-2021-0073212 A      6/2021

OTHER PUBLICATIONS

CN-109149997-A_translate (Year: 2019).*
Lee, Jeong Hwan, et al. "High power flexible device through development of materials" *DBPIA*, Proceedings of the 2016 Fall Conference of the Institute of Electronic Engineers, Advanced Material Science and Engineering Sungkyunkwan University, 2016, (4 pages in Korean with English Abstract).

* cited by examiner

*Primary Examiner* — Tulsidas C Patel
*Assistant Examiner* — Mohammed Ahmed Qureshi
(74) *Attorney, Agent, or Firm* — NSIP Law

(57) ABSTRACT

The present invention relates to an ultrasonic wave-driven triboelectric generator in which a self-gap is formed using plasma etching. The present invention relates to an ultrasonic wave-driven triboelectric generator having a polymer film as one triboelectric layer having a self-gap defined therein using plasma etching such that a surface area thereof is increased to achieve high power and miniaturization of the generator.

12 Claims, 5 Drawing Sheets

Conventional ultrasonic wave-driven triboelectric generator

Ultrasonic wave-driven triboelectric generator having gap

Gapless ultrasonic wave-driven triboelectric generator

ULTRASONIC WAVE-DRIVEN TRIBOELECTRIC GENERATOR WITH SELF-GAP FORMED USING PLASMA ETCHING

CROSS-REFERENCE TO RELATED APPLICATION

This application claims priority from Korean Patent Application No. 10-2021-0146182 filed on Oct. 29, 2021 in the Korean Intellectual Property Office, and all the benefits accruing therefrom under 35 U.S.C. 119, the contents of which in its entirety are herein incorporated by reference.

BACKGROUND

Field

The present disclosure relates to an ultrasonic wave-driven triboelectric generator in which a self-gap is formed using plasma etching. The present disclosure relates to an ultrasonic wave-driven triboelectric generator having a polymer film as one triboelectric layer having a self-gap defined therein using plasma etching such that a surface area thereof is increased to achieve high power and miniaturization of the generator.

Description of Related Art

Recently, as we enter an aging society, demand for implantable medical devices is increasing. Currently, a commercially available implantable medical device generates an electrical signal from a power source composed of a battery and a circuit. A conventional neurostimulator using a battery has a limited lifespan and has limitations in reducing a volume of the device or changing its shape. For this reason, ultrasound-based nerve stimulation and regeneration technology has been developed, but has limitations in commercialization thereof.

In order to reduce discomfort of a patient and facilitate a surgical operation, miniaturization of the device is essential. In an ultrasonic-driven triboelectric energy generator, as an active area of the device decreases, an output thereof decreases. Thus, there is a limit in reducing a size of the device. In addition, in order to insert the device into the patient and operate the device for a long period of time, it is necessary to package the device with a proven material such as titanium. However, due to an attenuation effect of ultrasonic wave by titanium, it is difficult to generate sufficient output when the device is housed in the titanium package.

According to the problems of the prior art as described above, there is a need for an ultra-small ultrasonic wave-driven triboelectric energy generator capable of securing electric power for nerve stimulation and regeneration while being housed in the titanium package.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

A purpose of the present disclosure is to propose a technology for increasing output using plasma etching on a polymer surface to implement a miniaturized ultrasonic-driven nerve stimulation and regeneration device to which a titanium package is applied. When the plasma etching process is applied to the polymer surface, this may bring about an effect of overcoming the existing limitations and offsetting an effect of reducing the output due to the titanium package and miniaturization to increase the output. Development of the smaller sized ultrasound-based triboelectric generator housed the titanium package may overcome the limitations of the existing device and contribute to the commercialization of the ultrasound-based neurostimulator.

Purposes in accordance with the present disclosure are not limited to the above-mentioned purpose. Other purposes and advantages in accordance with the present disclosure as not mentioned above may be understood from following descriptions and more clearly understood from embodiments in accordance with the present disclosure. Further, it will be readily appreciated that the purposes and advantages in accordance with the present disclosure may be realized by features and combinations thereof as disclosed in the claims.

A first aspect of the present disclosure provides an ultrasonic wave-driven triboelectric generator having a self-gap formed using plasma etching, the ultrasonic wave-driven triboelectric generator comprising: a first triboelectric layer made of a conductive material and serving as a first electrode; a second triboelectric layer disposed to face a frictional face of the first triboelectric layer, wherein the second triboelectric layer has a frictional face treated with plasma etching; and a package surrounding at least a portion of the first triboelectric layer and the second triboelectric layer, wherein the frictional face of the second triboelectric layer is plasma-etched so as to have a surface roughness such that a predefined spacing is defined between the first and second triboelectric layers, wherein when the ultrasonic wave is applied to the generator, the first triboelectric layer and the second triboelectric layer repeatedly contact and are spaced from each other to generate triboelectric energy.

In one implementation of the first aspect, the first triboelectric layer and the second triboelectric layer are spaced apart from each other.

In one implementation of the first aspect, the second triboelectric layer is made of a polymer material.

In one implementation of the first aspect, the generator further comprises a second electrode on a face opposite to the frictional face of the second triboelectric layer.

A second aspect of the present disclosure provides an ultrasonic wave-driven triboelectric generator having a self-gap formed using plasma etching, the ultrasonic wave-driven triboelectric generator comprising: a first triboelectric layer having a frictional face; a first electrode disposed on a face opposite to the frictional face of the first triboelectric layer; a second triboelectric layer disposed to face the frictional face of the first triboelectric layer, wherein the second triboelectric layer has a frictional face treated with plasma etching; and a package surrounding at least a portion of the first triboelectric layer and the second triboelectric layer, wherein the frictional face of the second triboelectric layer is plasma-etched so as to have a surface roughness such that a predefined spacing is defined between the first and second triboelectric layers, wherein when the ultrasonic wave is applied to the generator, the first triboelectric layer and the second triboelectric layer repeatedly contact and are spaced from each other to generate triboelectric energy.

In one implementation of the second aspect, the first triboelectric layer and the second triboelectric layer are spaced apart from each other.

In one implementation of the second aspect, the second triboelectric layer is made of a polymer material.

In one implementation of the second aspect, the generator further comprises a second electrode on a face opposite to the frictional face of the second triboelectric layer.

A third aspect of the present disclosure provides a therapeutic device insertable into a human body, wherein the device includes the ultrasonic wave-driven triboelectric generator having the self-gap formed using plasma etching according to the first aspect.

In one implementation of the third aspect, when an external ultrasonic wave is applied to the device inserted into the human body, the ultrasonic wave-driven triboelectric generator generates electric power.

A fourth aspect of the present disclosure provides a therapeutic device insertable into a human body, wherein the device includes the ultrasonic wave-driven triboelectric generator having the self-gap formed using plasma etching according to the second aspect.

In one implementation of the fourth aspect, when an external ultrasonic wave is applied to the device inserted into the human body, the ultrasonic wave-driven triboelectric generator generates electric power.

Effects in accordance with the present disclosure may be as follows but may not be limited thereto.

According to the present disclosure, the present technique may overcome the limitations of the existing ultrasonic wave-driven triboelectric energy generator, and may employ the titanium package and may achieve the miniaturization, and may generate sufficient output for nerve stimulation and regeneration.

In addition to the effects as described above, specific effects in accordance with the present disclosure will be described together with the detailed description for carrying out the disclosure.

BRIEF DESCRIPTION OF DRAWINGS

FIG. 6 is an SEM image to identify a surface shape of the polymer film subjected to the plasma etching process.

DETAILED DESCRIPTIONS

Figure 1:
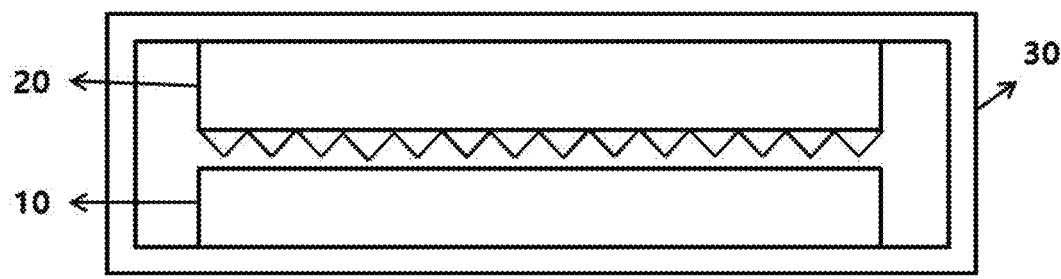
FIG. 1 and FIG. 2 are respective schematic diagrams of an ultrasonic wave-driven triboelectric generator in which a self-gap is formed using plasma etching according to an embodiment of the present disclosure.

For simplicity and clarity of illustration, elements in the drawings are not necessarily drawn to scale. The same reference numbers in different drawings represent the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure. Examples of various embodiments are illustrated and described further below. It will be understood that the description herein is not intended to limit the claims to the specific embodiments described. On the contrary, it is intended to cover alternatives, modifications, and equivalents as may include within the idea and scope of the present disclosure as defined by the appended claims.

A shape, a size, a ratio, an angle, a number, etc. disclosed in the drawings for illustrating embodiments of the present disclosure are illustrative, and the present disclosure is not limited thereto. The same reference numerals refer to the same elements herein. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

The terminology used herein is for the purpose of describing particular embodiments only and is not intended to limit the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entirety of list of elements and may not modify the individual elements of the list. When referring to "C to D", this means C inclusive to D inclusive unless otherwise specified.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the idea and scope of the present disclosure.

In addition, it will also be understood that when a first element or layer is referred to as being present "on" or "beneath" a second element or layer, the first element may be disposed directly on or beneath the second element or may be disposed indirectly on or beneath the second element with a third element or layer being disposed between the first and second elements or layers. It will be understood that when an element or layer is referred to as being "connected to", or "coupled to" another element or layer, it may be directly on, connected to, or coupled to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

Further, as used herein, when a layer, film, region, plate, or the like may be disposed "on" or "on a top" of another layer, film, region, plate, or the like, the former may directly contact the latter or still another layer, film, region, plate, or the like may be disposed between the former and the latter. As used herein, when a layer, film, region, plate, or the like is directly disposed "on" or "on a top" of another layer, film, region, plate, or the like, the former directly contacts the latter and still another layer, film, region, plate, or the like is not disposed between the former and the latter. Further, as used herein, when a layer, film, region, plate, or the like may be disposed "below" or "under" another layer, film, region, plate, or the like, the former may directly contact the latter or still another layer, film, region, plate, or the like may be disposed between the former and the latter. As used herein, when a layer, film, region, plate, or the like is directly disposed "below" or "under" another layer, film, region, plate, or the like, the former directly contacts the latter and still another layer, film, region, plate, or the like is not disposed between the former and the latter.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In one example, when a certain embodiment may be implemented differently, a function or operation specified in a specific block may occur in a sequence different from that specified in a flowchart. For example, two consecutive blocks may actually be executed at the same time. Depending on a related function or operation, the blocks may be executed in a reverse sequence.

In descriptions of temporal relationships, for example, temporal precedent relationships between two events such as "after", "subsequent to", "before", etc., another event may occur therebetween unless "directly after", "directly subsequent" or "directly before" is not indicated. The features of the various embodiments of the present disclosure may be partially or entirely combined with each other, and may be technically associated with each other or operate with each other. The embodiments may be implemented independently of each other and may be implemented together in an association relationship. Spatially relative terms, such as "beneath," "below," "lower," "under," "above," "upper," and the like, may be used herein for ease of explanation to describe one element or feature's relationship to another element or feature as illustrated in the figures. It will be understood that the spatially relative terms are intended to encompass different orientations of the device in use or in operation, in addition to the orientation depicted in the figures. For example, when the device in the drawings may be turned over, elements described as "below" or "beneath" or "under" other elements or features would then be oriented "above" the other elements or features. Thus, the example terms "below" and "under" may encompass both an orientation of above and below. The device may be otherwise oriented, for example, rotated 90 degrees or at other orientations, and the spatially relative descriptors used herein should be interpreted accordingly.

Hereinafter, embodiments according to the technical idea of the present disclosure will be described with reference to the accompanying drawings.

The present disclosure relates to an ultrasonic wave-driven triboelectric generator in which a self-gap is formed using plasma etching. The present disclosure relates to an ultrasonic wave-driven triboelectric generator having a polymer film as one triboelectric layer having a self-gap defined therein using plasma etching such that a surface area thereof is increased to achieve high power and miniaturization of the generator. According to the present disclosure, the present technique may overcome the limitations of the existing ultrasonic wave-driven triboelectric energy generator, and may employ the titanium package and may achieve the miniaturization, and may generate sufficient output for nerve stimulation and regeneration.

Figure 5A:
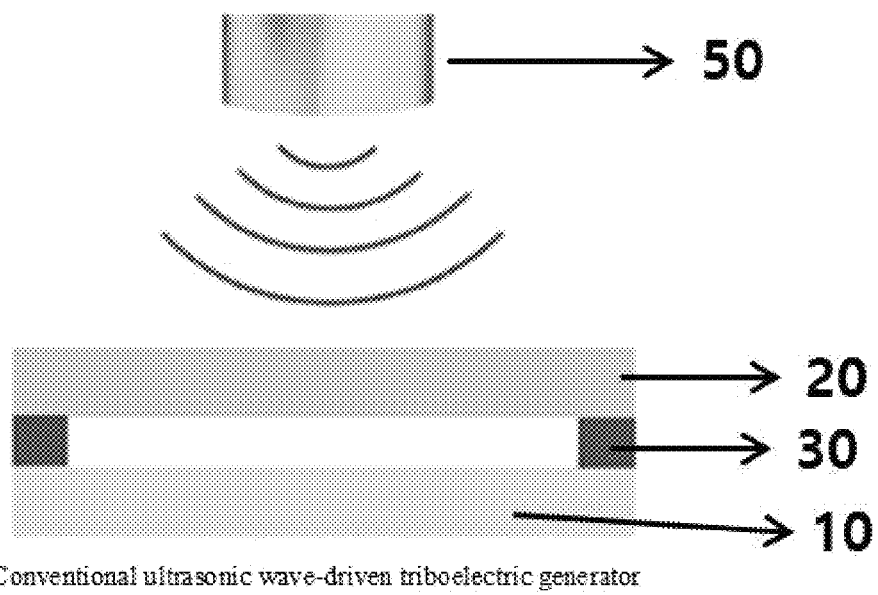
FIGS. 5A to 5C respectively show structures of a conventional ultrasonic wave-driven triboelectric generator, and an ultrasonic wave-driven triboelectric energy generator manufactured using a film subjected to a plasma etching process.
Figure 5B:
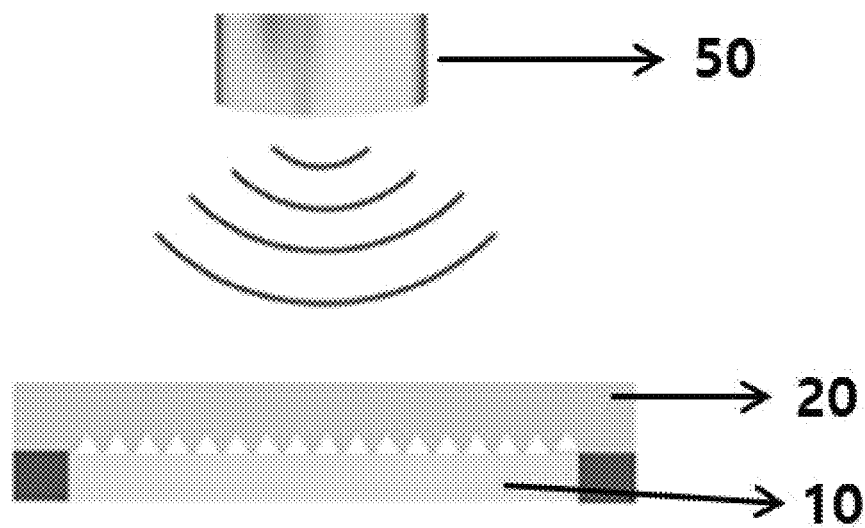
Figure 5C:
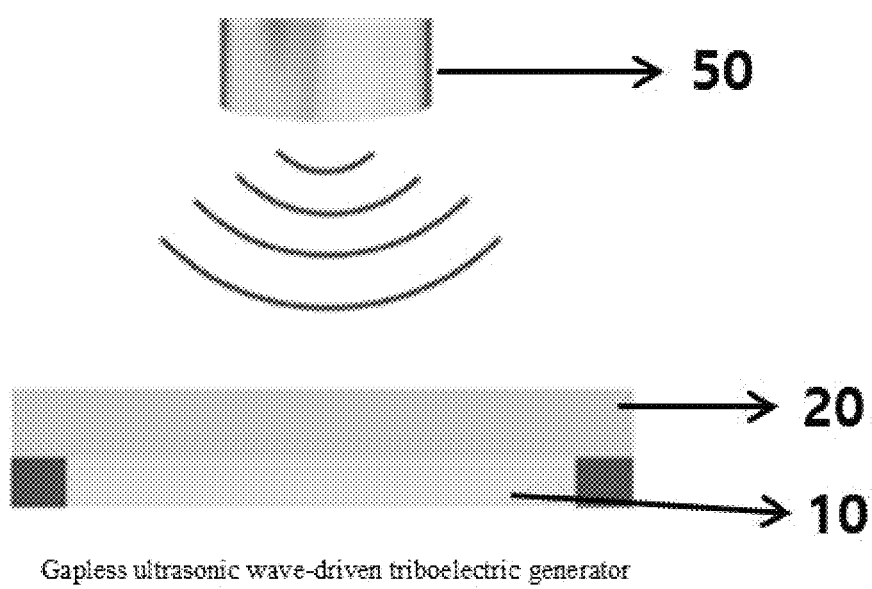

FIGS. 5A to 5C respectively show structures of a conventional ultrasonic wave-driven triboelectric generator, and an ultrasonic wave-driven triboelectric energy generator manufactured using a film subjected to a plasma etching process.

Referring to FIG. 5A, the conventional ultrasonic-based triboelectric generator obtains electrical energy by changing an electric field as a mechanical displacement changes and thus requires a predefined spacing between a polymer film and an electrode, and thus a spacer corresponding thereto.

However, referring to FIG. 5B, when the spacer is used, it is difficult to manufacture a device that exhibits a uniform output due to the limitation of maintaining the predefined spacing. To the contrary, when the spacer is not used, the spacing between the polymer film and the electrode is not secured, such that high power is not achieved.

According to the present disclosure based on FIG. 5C, when the polymer film as treated with a plasma etching process is used as a triboelectric layer having a frictional face of an ultrasonic wave-driven triboelectric energy generator, a frictional surface area is increased as well as a certain sized spacing between the polymer film and the electrode is formed (that is, the self-gap is formed), such that high output may be achieved in a very small device.

Figure 2:
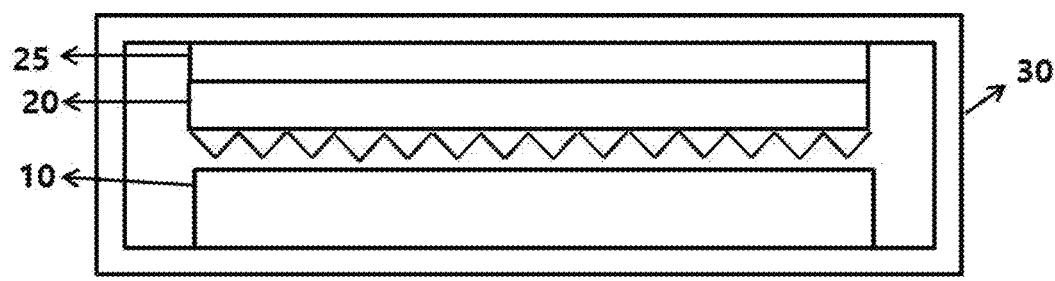

FIG. 1 and FIG. 2 show respective schematic diagrams of an ultrasonic wave-driven triboelectric generator in which a self-gap is formed using plasma etching according to an embodiment of the present disclosure.

Referring to FIG. 1, the ultrasonic wave-driven triboelectric generator in which the self-gap is formed using plasma etching according to an embodiment of the present disclosure includes a first triboelectric layer 10 made of a conductive material and acting as a first electrode; a second triboelectric layer 20 facing a frictional face of the first triboelectric layer and having a frictional face treated with plasma etching; and a package 30 surrounding at least a portion of the first triboelectric layer and the second triboelectric layer. In this case, it is obvious to those skilled in the art that positions of the first triboelectric layer and the second triboelectric layer are irrelevant to a feature of the device of the present disclosure.

Figure 3:
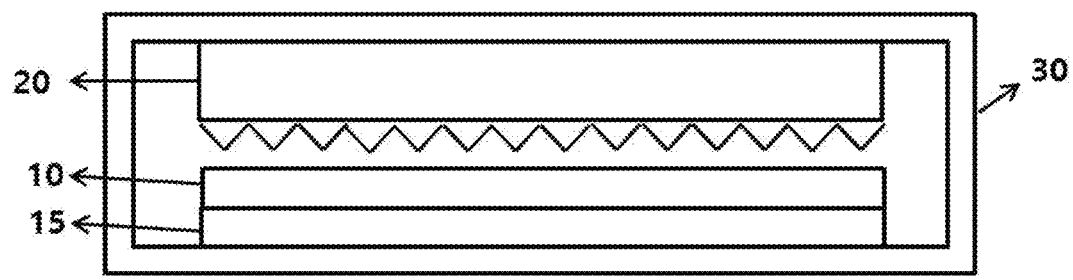
FIG. 3 and FIG. 4 are respective schematic diagrams of an ultrasonic wave-driven triboelectric generator in which a self-gap is formed using plasma etching according to a further embodiment of the present disclosure.
Figure 4:
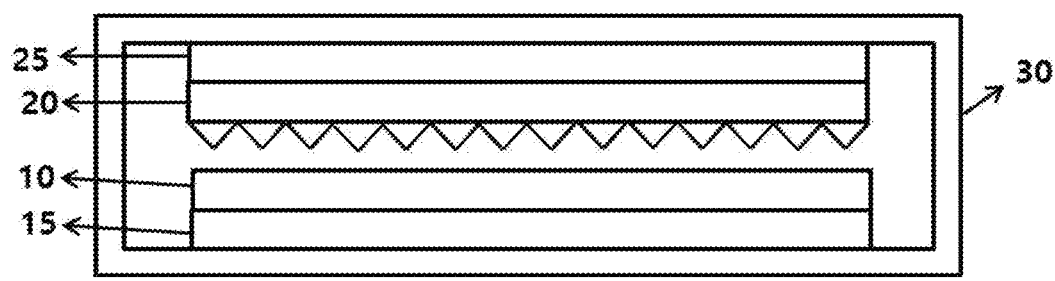

The first triboelectric layer 10 may be made of a conductive material capable of simultaneously performing a role of the first electrode as shown in FIG. 1. A case where the first triboelectric layer does not act as the first electrode and the generator has a separate first electrode is shown in FIG. 3 and FIG. 4.

The second triboelectric layer 20 is disposed to face the frictional face of the first triboelectric layer, and has the frictional face which is treated with plasma-etching. The second triboelectric layer 20 is made of a plasma etching-treated polymer, for example, a polymer material such as perfluoroalkoxy alkane (PFA), polytetrafluoroethylene (PTFE), or polyvinylidene (PVDF) treated with plasma-etching.

The frictional face of the second triboelectric layer is plasma-etched so as to have a surface roughness as shown in the figure. Thus, the self-gap between the first and second triboelectric layers is formed, and at the same time, the surface friction area of the second triboelectric layer increases, thereby generating a high output in a very small device. The frictional surface is not smooth but uneven due to the plasma etching treatment. It is illustrated that the uneven frictional surface has a regular repetition of sawtooth shapes. However, the shape thereof is not necessarily limited thereto.

The package 30 surrounds at least a portion of the first triboelectric layer 10 and the second triboelectric layer 20. The package may be made of titanium. Thus, high chemical/electrical/mechanical stability may be secured using this titanium packaging.

When ultrasonic waves are applied to the ultrasonic wave-driven triboelectric generator in which the self-gap is formed using plasma etching in accordance with the present disclosure, the first triboelectric layer and the second triboelectric layer repeatedly contact each other and are removed from each other to generate triboelectric electricity.

In this case, the first triboelectric layer and the second triboelectric layer may be spaced apart from each other via the self-gap as described above. Alternatively, the first triboelectric layer and the second triboelectric layer may be spaced apart from each other without a self-gap effect.

Further, as shown in FIG. 2, the ultrasonic wave-driven triboelectric generator may further include a second electrode 25 disposed on a face opposite to the frictional face (a face facing the first triboelectric layer) of the second triboelectric layer 20.

FIG. 3 and FIG. 4 are respective schematic diagrams of an ultrasonic wave-driven triboelectric generator in which a self-gap is formed using plasma etching according to a further embodiment of the present disclosure.

In the embodiment of FIGS. 3 and 4, the first triboelectric layer is not made of a conductive material, and thus the generator further includes a separate first electrode 15, unlike the embodiment of FIGS. 1 and 2 in which the first triboelectric layer is made of the conductive material and thus serves as the first electrode. All contents of the embodiment of FIGS. 3 and 4 are the same as those of the embodiments of FIG. 1 and FIG. 2, except for the above difference. Thus, repeated descriptions will be omitted.

An ultrasonic wave-driven triboelectric generator in which a self-gap is formed using plasma etching according to the further embodiment of the present disclosure includes the first triboelectric layer 10, the first electrode 15 disposed on the opposite face to the frictional face of the first triboelectric layer 10, the second triboelectric layer 20 disposed to face the frictional face of the first triboelectric layer and having a frictional face treated with plasma etching, and the package 30 surrounding at least a portion of the first triboelectric layer and the second triboelectric layer.

The frictional face of the second triboelectric layer is plasma etched so as to have the surface roughness such that a predetermined spacing between the first and second triboelectric layers is formed.

The second triboelectric layer 20 is disposed to face the frictional face of the first triboelectric layer, and has the frictional face which is treated with plasma-etching. The second triboelectric layer 20 is made of a plasma etching-treated polymer, for example, a polymer material such as perfluoroalkoxy alkane (PFA), polytetrafluoroethylene (PTFE), or polyvinylidene (PVDF) treated with plasma-etching.

The package 30 surrounds at least a portion of the first triboelectric layer 10 and the second triboelectric layer 20. The package may be made of titanium. Thus, high chemical/electrical/mechanical stability may be secured using this titanium packaging.

When ultrasonic waves are applied to the ultrasonic wave-driven triboelectric generator in which the self-gap is formed using plasma etching in accordance with the present disclosure, the first triboelectric layer and the second triboelectric layer repeatedly contact each other and are removed from each other to generate triboelectric electricity.

In this case, the first triboelectric layer and the second triboelectric layer may be spaced apart from each other via the self-gap as described above. Alternatively, the first triboelectric layer and the second triboelectric layer may be spaced apart from each other without a self-gap effect.

Further, as shown in FIG. 4, the ultrasonic wave-driven triboelectric generator may further include the second electrode 25 disposed on a face opposite to the frictional face (a face facing the first triboelectric layer) of the second triboelectric layer 20.

Figure 6:
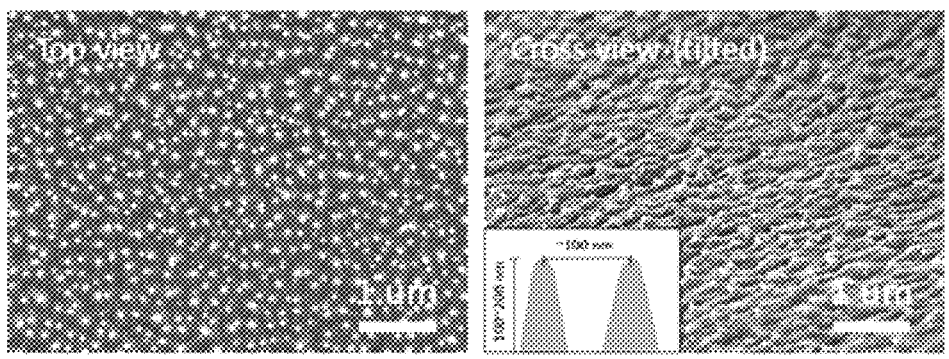
FIG. 6 shows a surface shape of a film to which a plasma etching process is applied.

A human body implantable therapeutic device may include the ultrasonic wave-driven triboelectric generator in which the self-gap is formed using plasma etching according to the embodiment of the present disclosure as described above. The human body implantable therapeutic device may be implanted into the human body. When an external ultrasonic wave is applied thereto, the ultrasonic wave-driven triboelectric generator may generate the electric power. The therapeutic device may be used, for example, for nerve stimulation and nerve treatment as shown in FIG. 6.

The ultrasonic wave-driven triboelectric generator in which the self-gap is formed using plasma etching according to the embodiment of the present disclosure as described above may act as a component which may be implanted into the human body. Thus, the ultrasonic wave-driven triboelectric generator may be made of a material having biodegradable or time-limited properties inside the human body.

A material of each of the electrodes according to the present disclosure may include a biodegradable metal or conductive polymer. Examples of the biodegradable metal may include, but are not limited to, a metal material such as Mg and Mo that may be decomposed in a living body.

Further, the package according to the present disclosure may be made of a porous time-limited material. The porous time-limited material may include, for example, a porous biodegradable polymer such as PHBV, PLA, PCL, etc. However, the present disclosure is not limited thereto.

When the ultrasonic wave is applied to the porous time-limited material, an ultrasonic wave energy is concentrated into an air layer in a matrix of the porous material due to a large difference between an acoustic wave resistance of the air layer and an acoustic wave resistance of the matrix of the porous material. However, when an ultrasonic wave with a low intensity is applied thereto, the matrix is not decomposed because the ultrasonic wave energy concentrated into the air layer of the porous material is not large. On the contrary, when an ultrasonic wave with high intensity but non-harmless to the human body is applied thereto, the ultrasonic wave energy concentrated into the air layer is large, so that a pressure caused by the acoustic wave is applied to the matrix of the porous material, such that a portion of the porous time-limited material around the air layer is decomposed.

In accordance with the present disclosure using the above principle, the package made of the porous time-limited material may be made of an ultrasonic wave selective reaction time-limited material. Thus, when the charging device has been inserted into the human body, the ultrasonic wave having a low intensity is applied to the triboelectric energy generating device of the charging device to generate the electric field to maintain the polarized state. After completion of use thereof, the triboelectric energy generating device may be biodegraded inside the human body by applying ultrasonic wave with high intensity thereto. That is, the porous time-limited material may be the ultrasonic wave selective reaction time-limited material that may be decomposed when the ultrasonic wave with an intensity greater than or equal to a critical intensity at which the decomposition thereof starts is applied to the device. When the ultrasonic wave having the intensity lower than the critical intensity is applied to the device, the first and second triboelectric layers repeatedly contact and are spaced from each other via the application of the ultrasonic wave to generate the triboelectric energy. When the ultrasonic wave having the intensity greater than or equal to the critical intensity is applied thereto, the package made of the porous time-limited material may be decomposed.

An ultrasonic wave transducer 50 in FIG. 5A to 5C may generate an ultrasonic wave and transmit the generated ultrasonic wave to the triboelectric energy generating device. In general, for medical treatment, a frequency of the ultrasonic wave is in a range of about 20 kHz to 50 kHz, and an intensity of the ultrasonic wave is in a range of about 1 W/cm$^2$. In this case, the critical intensity of the ultrasonic wave at which the porous time-limited material is decomposed may be in a range of about 3 W/cm$^2$ to 5 W/cm$^2$.

Hereinafter, the present disclosure will be additionally described along with specific examples. However, the present disclosure is not limited thereto.

Example 1

FIGS. 5A to 5C respectively show structures of a conventional ultrasonic wave-driven triboelectric generator, and an ultrasonic wave-driven triboelectric energy generator manufactured using a film subjected to a plasma etching process.

The generator according to an embodiment of the present disclosure, as shown in FIG. 5C include the first triboelectric layer 10 made of gold (Au); and the second triboelectric layer 20 made of plasma-etched perfluoroalkoxy alkane (PFA). The plasma etching was performed for 10 minutes at 100 W under O$_2$ and Ar atmosphere. Although not shown, the ultrasonic-based triboelectric energy generator having a size of 5 mm×5 mm of an active area and enclosing the titanium package the first and second triboelectric layers was manufactured.

FIG. 6 shows a surface shape of a film to which a plasma etching process is applied. FIG. 6 is an SEM image to identify a surface shape of the polymer film subjected to the plasma etching process.

Figure 7:
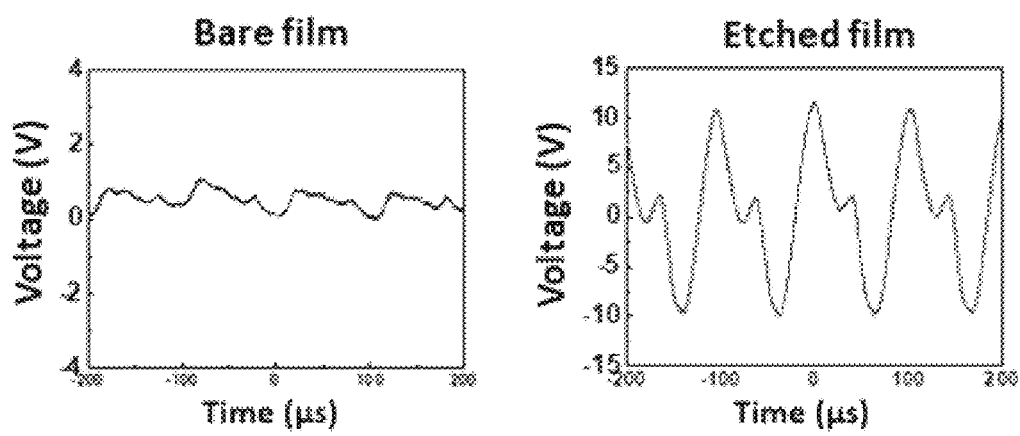
FIG. 7 shows a comparison between an output of a device using a polymer film not subjected to surface treatment an output of a device using a film to which a plasma etching process is applied.

FIG. 7 shows data of a measured voltage generated from each of a device including a polymer film not subjected to surface treatment and a device including a polymer film subjected to a plasma etching process when after the device with a size of 5 mm×5 mm of the active area is bonded to titanium and then an ultrasonic wave having a frequency of 20 kHz at an intensity of 1 W/cm$^2$ is applied to the device. Based on the data of FIG. 7, it is identified that the device including a polymer film not subjected to surface treatment generates 529 mV based on a RMS value, while the device including the film to which the plasma etching process was applied generates 6.115 V based on a RMS value. Thus, it is identified that the energy conversion efficiency increases by about 11 times when the plasma etching process is applied.

Figure 8:
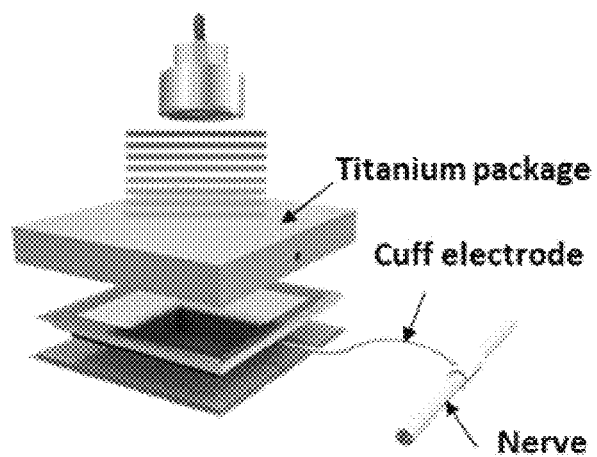
FIG. 8 shows a schematic diagram of nerve stimulation using an ultrasonic wave-driven triboelectric energy generator manufactured using a film subjected to a plasma etching process.

FIG. 8 shows a schematic diagram of nerve stimulation using an ultrasonic wave-driven triboelectric energy generator manufactured using a film subjected to a plasma etching process.

Packaging using titanium and miniaturization are essential for practical use of the ultrasonic wave-driven triboelectric energy generator. In accordance with the present disclosure, an ultra-small device to which the titanium package is applied as an energy source for nerve stimulation and regeneration. Thus, the ultrasonic wave-driven triboelectric energy generator in accordance with the present disclosure may reduce physical discomfort and mental burden of the patient and may simplify the surgical process and thus is meaningful in terms of commercialization.

The descriptions of the presented embodiments have been provided so that a person of ordinary skill in the art of any the present disclosure may use or practice the present disclosure. Various modifications to these embodiments will be apparent to those skilled in the art of the present disclosure, and the general principles defined herein may be applied to other embodiments without departing from the scope of the present disclosure. Thus, the present disclosure is not intended to be limited to the embodiments presented herein, but is to be construed in the widest scope consistent with the principles and novel features presented herein.

What is claimed is:

1. An ultrasonic wave-driven triboelectric generator having a self-gap formed by plasma etching, the ultrasonic wave-driven triboelectric generator comprising:
    a first triboelectric layer made of a conductive material and serving as a first electrode;
    a second triboelectric layer disposed to face a frictional face of the first triboelectric layer, wherein the second triboelectric layer has a frictional face treated by plasma etching; and
    a package made of titanium and surrounding at least a portion of the first triboelectric layer and the second triboelectric layer,
    wherein the frictional face of the second triboelectric layer is plasma-etched to have a surface roughness such that there is a predefined gap between the first and second triboelectric layers, and
    wherein when an ultrasonic wave is applied to the generator, the first triboelectric layer and the second triboelectric layer repeatedly contact each other and separate from each other to generate triboelectric energy.

2. The ultrasonic wave-driven triboelectric generator of claim 1, wherein the first triboelectric layer and the second triboelectric layer are spaced apart from each other, and
    wherein the frictional face of the second triboelectric layer comprises a sawtooth shape that repeats at regular intervals.

3. The ultrasonic wave-driven triboelectric generator of claim 1, wherein the second triboelectric layer is made of a polymer material.

4. The ultrasonic wave-driven triboelectric generator of claim 1, wherein the generator further comprises a second electrode on a face opposite to the frictional face of the second triboelectric layer.

5. An ultrasonic wave-driven triboelectric generator having a self-gap formed by plasma etching, the ultrasonic wave-driven triboelectric generator comprising:
- a first triboelectric layer having a frictional face;
- a first electrode disposed on a face opposite to the frictional face of the first triboelectric layer;
- a second triboelectric layer disposed to face the frictional face of the first triboelectric layer, wherein the second triboelectric layer has a frictional face treated by plasma etching; and
- a package made of titanium and surrounding at least a portion of the first triboelectric layer and the second triboelectric layer,
- wherein the frictional face of the second triboelectric layer is plasma-etched to have a surface roughness such that there is a predefined gap between the first and second triboelectric layers, and
- wherein when an ultrasonic wave is applied to the generator, the first triboelectric layer and the second triboelectric layer repeatedly contact each other and separate from each other to generate triboelectric energy.

6. The ultrasonic wave-driven triboelectric generator of claim 5, wherein the first triboelectric layer and the second triboelectric layer are spaced apart from each other, and
wherein the frictional face of the second triboelectric layer comprises a sawtooth shape that repeats at regular intervals.

7. The ultrasonic wave-driven triboelectric generator of claim 5, wherein the second triboelectric layer is made of a polymer material.

8. The ultrasonic wave-driven triboelectric generator of claim 5, wherein the generator further comprises a second electrode on a face opposite to the frictional face of the second triboelectric layer.

9. A therapeutic device insertable into a human body and comprising an ultrasonic wave-driven triboelectric generator having a self-gap formed by plasma etching, the ultrasonic wave-driven triboelectric generator comprising:
- a first triboelectric layer made of a conductive material and serving as a first electrode;
- a second triboelectric layer disposed to face a frictional face of the first triboelectric layer, wherein the second triboelectric layer has a frictional face treated by plasma etching; and
- a package made of titanium and surrounding at least a portion of the first triboelectric layer and the second triboelectric layer,
- wherein the frictional face of the second triboelectric layer is plasma-etched to have a surface roughness such that there is a predefined gap between the first and second triboelectric layers, and
- wherein when an ultrasonic wave is applied to the generator, the first triboelectric layer and the second triboelectric layer repeatedly contact and separate from each other to generate triboelectric energy.

10. A therapeutic device insertable into a human body, wherein the therapeutic device comprises the ultrasonic wave-driven triboelectric generator of claim 5.

11. The therapeutic device of claim 9, wherein when the ultrasonic wave is applied to the device inserted into the human body, the ultrasonic wave-driven triboelectric generator is configured to generate electric power.

12. The therapeutic device of claim 10, wherein when the ultrasonic wave is applied to the device inserted into the human body, the ultrasonic wave-driven triboelectric generator is configured to generate electric power.

* * * * *